(12) United States Patent
Patel et al.

(10) Patent No.: US 6,828,119 B2
(45) Date of Patent: Dec. 7, 2004

(54) ENZYMATIC DEPROTECTION OF AMINES AND HYDROXIDES

(75) Inventors: Ramesh Patel, Bridgewater, NJ (US); David Brzozowski, Piscataway, NJ (US); Venkata Nanduri, East Brunswick, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 217 days.

(21) Appl. No.: 10/017,711

(22) Filed: Dec. 14, 2001

(65) Prior Publication Data

US 2002/0123110 A1 Sep. 5, 2002

Related U.S. Application Data

(60) Provisional application No. 60/259,715, filed on Jan. 4, 2001.

(51) Int. Cl.$^7$ .............................. C12P 1/00; C12P 13/04; C12P 17/12
(52) U.S. Cl. ........................... 435/41; 435/106; 435/117
(58) Field of Search ............................ 435/41, 106, 117

(56) References Cited

U.S. PATENT DOCUMENTS

| | | | | |
|---|---|---|---|---|
| 4,182,654 A | * | 1/1980 | Royer ........................ | 435/272 |
| 5,508,272 A | | 4/1996 | Robl | |
| 5,532,149 A | * | 7/1996 | Briggs et al. ................ | 435/122 |
| 5,552,397 A | | 9/1996 | Karanewsky et al. | |
| 5,625,030 A | * | 4/1997 | Williams et al. ............. | 528/361 |
| 5,814,616 A | * | 9/1998 | Srivastava et al. ............ | 514/42 |
| 5,981,267 A | * | 11/1999 | Wong et al. ................. | 435/280 |

FOREIGN PATENT DOCUMENTS

WO      WO00/47207      8/2000

OTHER PUBLICATIONS

Turkiewicz et al., "Biosynthesis and Properties of an Extracellular Metalloprotease from the Antarctic Marine Bacterium *Sphingomonas paucimobilis*" (1999) J. Biotechnol., 70, 53–60.*
Schinner et al., "Extracellular Protease–Producing Psychrotrophic Bacteria from High Alpine Habitats" (1992) Actic and Alpine Research, 24(1), 88–92.*
Reidel et al., "Unzymatic Protecting Group Techniques in Bioorganic Synthesis" (1993) J. Prakt. Chem., 335(2), 109–127.*
Meyers et al., "Enzymes as Reagents in Peptide Synthesis. Enzymic Removal of Amine Protecting Groups" (1975) Proc. Nat. Acad. Sci. USA, 72(6), 2193–2196.*
Schinner et al., "Extracellular Protease–Producing Psychrotrophic Bacteria from High Alpine Habitats" (1991) Arctic and Alpine Research, vol. 24, No. 1, pp. 88–92, Abstract in CABA, AN 92:56751.*
Turkiewicz et al., "Biosynthesis and Properties of an Extracellular Metalloprotease from the Antarctic Marine Bacterium *Sphingomonas paucimobilis*" (1999) Progress in industrial Microbiology, 35, 53–60, Abstract in CAPLUS, AN 2001:30729.*
Jeyaraj et al., Tetrahedron Letters 42 (2001) pp. 835–837.
Pohl et al., J. Am. Chem. Soc. 119, (1997) pp. 6702–6710.
Kappes et al., Carbohydrate Research 305 (1998) pp. 341–349.
Pohl et al., Tetrahedron Letters, vol. 36, No. 17, (1985) pp. 2963–2966.
Theodoridis, G., Tetrahedron 56 (2000) pp. 2239–2358.
Waldmann et al., 277 Chemical Reviews, American Chemical Society, 94 (1994) Jun., No. 4, pp. 911–937.
Green and Wuts, Protective Groups In Organic Synthesis, John Wiley & Sons, NY, 1991. pp. 307–348.
Matsumura et al., Chem. Pharm. Bull., vol. 33, No. 1, pp. 408–411 (1985).
Matsumura et al., Chem. Pharm. Bull., vol. 33, No. 4, pp. 1739–1744 (1985).
Murao et al., Agric. Biol., vol. 49, No. 4, pp. 967–972 (1985).
Matsumura et al., Agric. Biol. Chem., vol. 49, No. 4, pp. 973–979 (1985).
Matsumura et al., Agric. Biol. Chem., vol. 49, No. 12, pp. 3343–3345 (1985).
Matsumura et al., Agric. Biol. Chem., vol. 50, No. 6, pp. 1563–1571 (1986).
Oshiro et al., Appl. Microbial. Biotechnol., vol. 48, No. 4, pp. 546–548 (1997).
Holland et al., Monatshefte fur Chemie, vol. 131, No. 6, pp. 667–672 (2000).

* cited by examiner

*Primary Examiner*—Jon P Weber
(74) *Attorney, Agent, or Firm*—Terence J. Bogie; Stephen B. Davis

(57) ABSTRACT

Provided is a method of deprotecting a hydroxide or amine protected with a group of formula

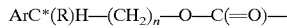

ArC*(R)H—(CH$_2$)$_n$—O—C(=O)— where the substituents are as described below, the method comprising: contacting the protected hydroxide or amine with an enzyme effective to remove the protecting group; and recovering the amine. Also provided is a method of isolating a bacteria producing an enzyme effective to remove a protecting group comprising: growing prospective bacteria on a medium having a growth selective amount of an amine compound that is protected as above; and isolating bacteria that grow on said medium.

27 Claims, No Drawings

ENZYMATIC DEPROTECTION OF AMINES AND HYDROXIDES

This application is related to, and pursuant to 35 U.S.C. § 119(e) claims the benefit of priority of U.S. application Ser. No. 60/259,715, filed Jan. 4, 2001.

The present invention relates to mild, enzyme driven methods for removing amine and hydroxide protecting groups.

N-carbobenzyloxy (N-CBZ) group is commonly used to protect amino and hydroxide groups during organic synthesis. Other similar "carbamate" protecting groups are also used to protect amino groups. Chemical deprotection is usually achieved by methods such as hydrogenation with Palladium catalyst. However, if other groups are present that are susceptible to the deprotection condition (for example, sulfur during hydrogenation), alternative methods of deprotection are necessary. It has now been discovered that microorganisms can be readily isolated from soil samples using a selection technique of the invention to produce an enzyme activity effective to specifically release such protecting groups. Thus, an enzymatic method of deprotection conducted under mild conditions (e.g., aqueous medium at room temperature and atmospheric pressure) can be used which avoids damaging any susceptible or potentially susceptible groups.

SUMMARY OF THE INVENTION

The invention provides a method of deprotecting a hydroxide or amine protected with a group of formula

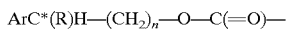

where the substituents are as described below, the method comprising: contacting the protected hydroxide or amine with an enzyme effective to remove the protecting group; and recovering the amine. Also provided is a method of isolating a bacteria producing an enzyme effective to remove a protecting group comprising: growing prospective bacteria on a medium having a growth selective amount of an amine compound that is protected as above; and isolating bacteria that grow on said medium.

The invention further provides a method of resolving a desired enantiomer of an amine or hydroxide linked to a chiral carbon. The amine or hydroxide protected with such a group is stereo-specifically hydrolyzed with the method of the invention. The desired enantiomer is either that hydrolyzed or that resistant to hydrolysis.

In one embodiment, the contacting step effectuates the following reaction:

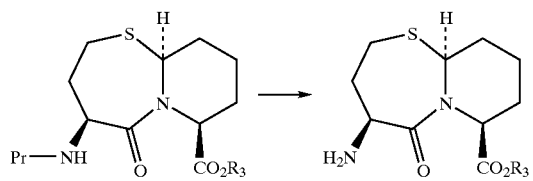

where Pr— is the above-described protecting group. In another embodiment, the contacting effectuates the following reaction:

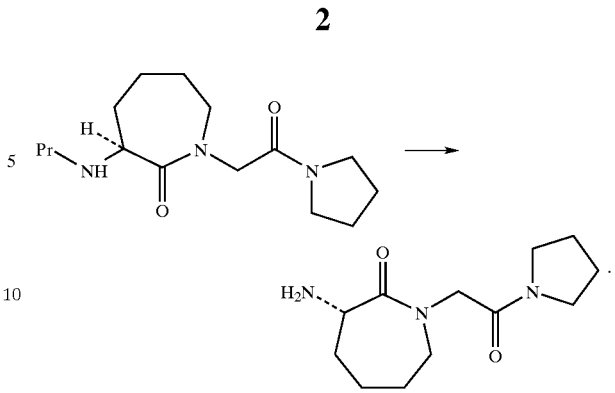

In yet another embodiment, the contacting effectuates the following reaction:

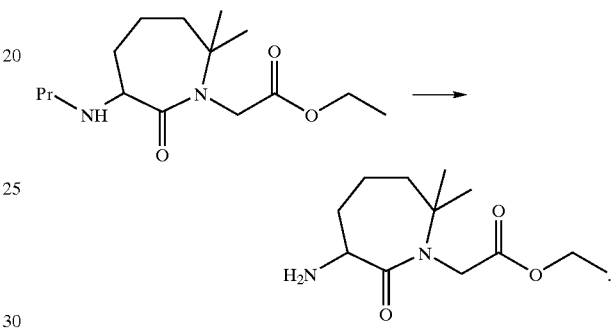

DETAILED DESCRIPTION OF THE INVENTION

The invention can be used to remove a number of carbamate protecting groups, of formula

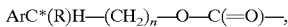

where R is H or independently the same as Ar, and n is 0 or 1–4. Ar refers to an aromatic or heteroaromatic ring with 5 to 6 ring atoms and one to two heteroatoms selected from O, N or S, Ar may be substituted with amino, alkanoyloxy, alkoxy, alkyl, alkylamino, allyl, carboxy, cycloalkyl, halo, haloalkyl, hydroxy, hydroxyalkyl or nitro, or up to one group which is (a) Ar* which is independently the same as Ar except that it is not substituted with a further aryl, (b) Ar*-alkyl- or (c) Ar*O—. A ring atom of Ar adjacent to C* can be substituted with —CH$_2$—, —O—, —NH—, —S(O)$_q$— or —P(O)$_r$—, to form a bridge to a corresponding position on R when R is Ar, wherein q is 0 or 1–2 and r is 0 or 1–2. In one embodiment, n is 0 when R is H. In another embodiment, n is 1 where R is the same as Ar. As illustrated by the Examples (see Table 2), the method is stereospecific, and thus can be used for resolving racemic mixtures.

These protecting groups are illustrated by such compounds as 9-fluorenylmethyl carbamate, 9-(2-sulfo) fluorenylmethyl carbamate, 9-(2,7-dibromo)fluorenylmethyl carbamate, 2,7-di-t-butyl-[9-(10,10-dioxo-10,10,10,10-tetrahydrothioxanthyl)methyl carbamate, benzyl carbamate, p-methoxybenzyl carbamate, p-nitrobenzyl carbamate, p-bromobenzyl carbamate, p-chlorobenzyl carbamate, 2,4-dichlorobenzyl carbamate, 9-anthrylmethyl carbamate, diphenyl methyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate, m-nitrobenzyl carbamate, 3,5- dimethoxybenzyl carbamate, 3,4-dimethoxy-6-nitrobenzyl carbamate, S-benzyl thiocarbamate, p-cyanobenzyl carbamate, 2-furanylmethyl carbamate, 4-(trimethylammonium)benzyl carbamate and 2,4,6-trimethylbenzyl carbamate. Protecting groups such as these are described in standard texts such as Greene and Wuts, *Protective Groups in Organic Synthesis*, John Wiley & Sons, New York, 1991 (especially pp. 315–348).

Alkyl components of substitutions are $C_1$–$C_6$ or $C_2$–$C_6$ where a $C_1$ moiety is chemically inappropriate (e.g., for alkanoyl). Cycloalkyl radicals are $C_3$–$C_6$. Haloalkyl preferably refers to perhaloalkyl, and preferably trifluoromethyl. Halo is preferably chloro or fluoro.

In one embodiment, the carbamate protecting group is a phenylmethyloxycarbonyl group, where the phenyl can be substituted. Illustrated substitutions to the phenylmethyloxycarbonyl include, for example, those recited above for Ar.

A source of the enzyme used in the invention can be isolated as an isolated bacteria having the appropriate activity. The method of isolation is preferably selection by growth on a medium in which sufficient growth-supporting nitrogen can only be obtained from an amine compound in which the amine is protected by the carbamate protecting group in question, or related carbamate protecting group. The examples below illustrate that such bacteria can be isolated from very ordinary sources of bacteria, such as environmental or soil samples.

The examples below exemplify that the selection technique identified by the inventors is effective to isolate appropriate bacteria, and thereby an appropriate enzyme source, using ordinary experimentation. The examples are for bacteria isolated by selecting for growth with a nitrogen source that is CBZ-protected. However, this illustration confirms Applicants' understanding that appropriate enzymes can be collected without undue experimentation using the same approach with the protecting group matched to the protecting group sought to be removed.

Where the amine or hydroxide involved in the enzymatic removal is identified as the most likely candidate for a cause of a proposed substrate being resistant to cleavage by a given enzyme, an appropriately protected version of that amine (or an analog, or an amine analog of the hydroxide) can be used to select another bacteria, and hence another enzyme. A collection of separate deprotecting enzymes or bacterial cultures each producing a useful enzyme can be stored and screened in the event that substitute enzymes are needed. Where the amine or hydroxide to be protected and deprotected is a complex molecule, with the amine or hydroxide portion linked to relatively distant moieties, then the amine model used in the selection process can be modeled on the portion of the complex adjacent to the amine or hydroxide. Preferably care is taken so that nearby moieties that in the complex molecule are derivatized are analogously derivatized.

As illustrated below, bacterial whole cells, extracts from whole cells, or purified enzyme preparations can be used to effect the deprotection provided by the invention. The enzyme acts catalytically so that small amounts are typically used, and as the impurities provided by enzyme sources (e.g., those of lesser purity) should not produce notable quantities of material that should behave like the intended product. Thus, impurities provided by the enzyme source are quickly selected against in post-reaction workup. In particular, where extracts are used, the impurities are by and large macromolecules; and since the typical intended products are typically not macromolecules, the impurities are quickly segregated away from the product.

Also as illustrated below, the substrate used in the enzyme selection process provides a facile tool for measuring enzyme activity, and hence for isolating the enzyme with selective microbiological enrichment and traditional protein chemistry techniques.

The amine or hydroxide protected by the protecting group can be any amine or hydroxide on any molecule. In many embodiments, the amine or hydroxide is found on a molecule that is of a size amenable to non-repetitive synthetic techniques. (Of course, the deprotection technique of the invention can also be used in repetitive techniques such as are used in peptide or nucleic acid synthesis.) In one preferred embodiment, the amine or hydroxide is part of a bioactive agent that is bioavailable to an animal after oral ingestion, or is part of a precursor to such a bioactive agent.

In one aspect, the amine is preferably an α- or β-amino acid, more preferably an α-amino acid.

The amine can be, for example, alanine, valine, leucine, isoleucine, proline, 4-hydroxyproline, phenylalanine, tryptophan, methionine, glycine, serine, homoserine, threonine, cysteine, homocysteine, tyrosine, asparagine, glutamine, aspartic acid, glutamic acid, lysine, α-amino-ε-caprolactam (lysine lactam), α-amino-δ,δ-dimethyl-ε-caprolactam, ε-methyllysine, ornithine, arginine, histidine or 3-methyhistidine, or any of the foregoing substituted on an alkyl portion thereof with hydroxy or alkyl, on an amino with up to one alkyl, or on a phenyl moiety substituted with the radicals recited above for Ar. Such an amino acid can be an L or D amino acid. Moreover, such amino acid can be derivatized to form a portion of a larger molecule via bonds formed by dehydration reactions with amine or carboxylic acid moieties, or by carbon-nitrogen bonds formed at the amine moieties.

Another class of alpha amino acids particularly useful in the invention are according to the following formula:

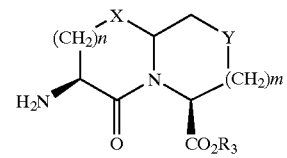

wherein: m is zero or one; Y is $CH_2$, S—(O)$_t$ or O provided that Y is S—(O)$_t$ or O only when m is one; X is S—(O)$_t$ or O; n is one or two; t is 0, 1 or 2; $R_3$ is hydrogen, alkyl, substituted alkyl, aryl-$(CH_2)_p$—; and p is 0 or 1–6. Of these amines, the following is a particularly preferred amine:

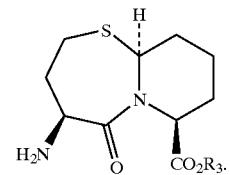

These compounds are described in more detail in U.S. Pat. No. 5,508,272. The teachings therein on making and using these compounds is incorporated by reference. Additional compounds of specific interest with respect to the use of this invention are described in WO 00/47207 and U.S. Pat. No. 5,552,397. The teachings on making and using the compounds described therein are incorporated by reference.

Protected amines or hydroxides are typically formed from reacting

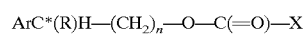

with the corresponding amines or hydroxides, where X is a leaving group (e.g., bromo, chloro, tosyl). The ArC*(R)H—(CH$_2$)$_n$—O—C(=O)—X is for example formed by reacting ArC*(R)H—(CH$_2$)$_n$—OH with phosgene, carbomyl diaidazole, triphosgene or a comparable reagents.

Definitions

The following terms shall have, for the purposes of this application, the respective meanings set forth below.

bioactive agent. A bioactive agent is a substance such as a chemical that can act on a cell, virus, tissue, organ or organism, including but not limited to insecticides or drugs (i.e., pharmaceuticals) to create a change in the functioning of the cell, virus, organ or organism. Preferably, the organism is a mammal, more preferably a human.

medium having a growth selective amount of an amine compound. A medium having a growth selective amount of a protected amine compound is a medium in which the amount of any other amines other than the amine compound is less than an amount effective to promote bacterial growth in a growth-mediated selection process. Preferably, the protected amine is essentially the sole nitrogen source.

EXAMPLE 1

Selective Techniques for Isolation of Microorganisms

A selective culture technique was used to isolate microorganisms that able to utilize N-α-CBZ-L-lysine as a sole source of nitrogen. Soil samples were collected from various sites in New Jersey. About a gram of soil samples suspended in 5 mL of water, mixed thoroughly and samples were allowed to settle. The supernatant solutions from various samples were inoculated in a medium A (2% glucose, 0.2% KH$_2$PO$_4$, 0.2% K$_2$HPO$_4$, 0.01% MgSO$_4$, 0.001% FeSO$_4$, 0.001% ZnSO$_4$, pH 7.0) containing 1% N-α-CBZ-L-lysine. After 4 days of growth when medium became turbid, cultures were transferred to the above medium containing 1.5% agar contained in petri plates. From this enrichment culture techniques eight different types of colonies were isolated. One culture (Z-2) was further identified as *Sphingomonas paucimobilis* strain and was deposited in American Type Culture Collection, Rockville, Md. as *Sphingomonas paucimobilis* strain ATCC 202027. This culture was used as a source of CBZ-deprotecting enzyme.

EXAMPLE 2

Growth of *Sphingomonas paucimobilis*

*Sphingomonas paucimobilis* was grown on N-α-CBZ-L-phenylalanine or [4S-(4α,7α,10aβ)]-Octahydro-5-oxo-4-[[(phenylmethoxy)carbonyl]amino]-7H-pyrido-[2,1-b][1,3] thiazepine-7-carbocylic acid, methyl ester (Compound A) as sole source of nitrogen. The *Sphingomonas paucimobilis* culture was inoculated in a medium A containing 1% N-α-CBZ-L-phenylalanine or 1% Compound A. After 2 days of growth, cultures were transferred to the medium A containing 1% N-α-CBZ-L-phenylalanine or 1% BMS199541, and 1.5% agar contained in petri plates. The colonies were isolated from the petri plates were grown in 100 mL of medium B (0.015% yeast extract, 2% glucose, 0.2% KH$_2$PO$_4$, 0.2% K$_2$HPO$_4$, 0.01% MgSO$_4$ and 0.2% NaCl, pH 7) containing 1% N-α-CBZ-L-phenylalanine and or 1% Compound A. Culture was grown at 28° C. and 280 RPM for 24 hours on a rotary shaker. Vials were prepared (1 mL culture in a 2 mL vial) from this culture and were stored at −70° C. for future use.

One vial (containing 1 mL of *Sphingomonas paucimobilis* in medium B) was used to inoculate 100 mL of medium B. Cultures were grown at 28° C. and 280 RPM for 48 hours on a rotary shaker. Cells were harvested by centrifugation at 18,000×g for 15 minutes, and stored at −70° C. until further use.

EXAMPLE 3

Biotransformation Using Whole Cells

In this process, the *Sphingomonas paucimobilis* was grown in 25 mL of medium B containing 25 mg of substrate (Compound A or CBZ-L-Phenylalanine) in a 250-mL flask. The flask was incubated at 28° C. and 250 rpm on a shaker. After 48 hours of biotransformation, the cells were removed by centrifugation. The supernatant containing the product [4S-(4α,7α,10aβ)]-Octahydro-5-oxo-4-amino-7H-pyrido-[2,1-b][1,3]thiazepine-7-carboxylic acid, methyl ester (Compound B) or L-Phenylalanine was analyzed by HPLC. The results are shown in the table 1.

TABLE 1

| Substrate | Product | % Conversion |
|---|---|---|
| Compound A | Compound B | 100 |
| CBZ-L-Phenylalanine | L-phenylaline | 100 |

HPLC Analysis

HPLC analysis was performed using a Hewlett-Packard (HP) 1090 instrument with a Vydac C-18 reverse phase column. The mobile phase solvent A containing 0.1% trifluoroacetic acid (TFA) in water and solvent B containing 0.1% TFA in 70% acetonitrile: 30% water. The following gradient of solvent A and B was used for the separation of substrates and products:

0 min: 100% A, 0–15 min: 50% B, 15–25 min: 100% B, 25–26 min: 0% B, and 26–30 min: 0%B. The flow rate was 1 mL/min. The column temperature was ambient, and the detection wavelength was at 215 nm. Under these conditions, the retention times for Compound A, Compound B, CBZ-L-Phenylalanine and L-Phenylalanine are 15.48 min., 7.28 min., 16.99 min. and 7.35 min., respectively. All other CBZ-containing compounds were also analyzed using these conditions.

EXAMPLE 4

Deprotection of CBZ Using Cell Extracts of *Sphingomonas paucimobilis* ATCC 202027

Preparation of Cell Extract of *Sphingomonas paucimobilis* ATCC 202027

Preparation of cell extracts were carried out at 4–7° C. Cells were washed with 50 mM potassium phosphate buffer, pH 7.0, and the washed cells (100 g) were suspended in 500 mL of buffer A (50 mM phosphate buffer, pH 7.0 containing 10% glycerol, and 2 mM DTT). To the cell suspensions, 1 mM phenylmethylsulfonyl fluoride (PMSF) solution in isopropanol was added. Cell suspensions (20% W/V, wet cells) were passed through a Microfluidizer (Microfluidics, Inc) at 12,000 psi (two passages) and disintegrated cells were centrifuged at 25,000×g for 30 min at 4° C. The supernatant solution obtained after centrifugation is referred to as cell extract.

CBZ-Deprotection Using Cell Extract

The cell extracts was used in deprotecting the CBZ-group from various compounds. It was useful in deprotecting CBZ-groups in various processes. Various D and L-CBZ-protected amino acids were incubated with the cell extract at 42° C. for 18–20 hours. The reactions were stopped by addition of 2 volumes of 50% acetonitrile containing 0.4% trifluro acetic acid (TFA). The results shown in table 2 indicate that the enzyme is specific in hydrolyzing the CBZ-group from CBZ-protected L-amino acids.

TABLE 2

| Substrate | Product | % Conversion |
| --- | --- | --- |
| N-α-CBZ-L-tyrosine | L-tyrosine | 100 |
| N-α-CBZ-D-tyrosine | D-tyrosine | 1.58 |
| O-α-CBZ-L-tyrosine | L-tyrosine | 100 |
| N-α-CBZ-L-Leucine | L-Leucine | 100 |
| N-α-CBZ-D-Leucine | D-Leucine | 1.2 |
| N-α-CBZ-L-phenylalanine | L-phenylalanine | 100 |
| N-α-CBZ-D-phenylalanine | D-phenylalanine | 0 |
| N-α-CBZ-L-Lysine | L-Lysine | 52 |
| N-ε-CBZ-D-Lysine | D-Lysine | 7 |
| N-α-ε-(CBZ)$_2$-L-Lysine | L-Lysine | 24 |
| N-α-CBZ-L-Proline | L-Proline | 100 |
| N-α-CBZ-D-Proline | D-Proline | 0 |
| Compound A | Compound B | 95 |

EXAMPLE 5

Purification of CBZ-Deprotecting Enzyme and the Use of Purified Enzyme in the Deprotection of CBZ-Group from Cbz-Containing Compounds Enzyme Assays Compound A or CBZ-phenylalanine at 0.5 mg was incubated with 0.4 mL of cell extract/fractions in 50 mM phosphate buffer, pH 7 at 45° C. for 18 hours. The reaction is stopped by the addition 1 ml of 50% acetonitrile containing 0.4% TFA. The samples were filtered and analyzed by HPLC for product and starting material.

Protein Assay

The Bio-Rad protein assay was used to determine protein concentration. The assay was performed according to the manufacturer (Bio-Rad) protocol.

Purification of the Enzyme

All the purification steps were carried out at room temperature. The purification of the enzyme was carried out using CBZ-L-phenylalanine as the substrate. The cell extract, prepared as above, was batch adsorbed with DEAE-cellulose (pre-equilibrated with buffer A) for 2 hours. The follow-through, which contained the active enzyme, was precipitated with ammonium sulfate (516 g/L) with constant stirring for 2 hours. The resulting precipitate obtained by centrifugation (15,000 rpm at 4° C.) was solubilized in buffer A containing 1M ammonium sulfate, loaded on to phenylsepharose (20 mL column which was pre-equilibriaiated with buffer A containing 1M ammonium sulfate). The column was sequentially washed with the buffer A containing 1M ammonium sulfate, 0.5M ammonium sulfate and 0.2M ammonium sulfate. Finally, the enzyme was eluted with buffer A. The fractions containing active enzyme were pooled (30 mL) and concentrated with Amicon PM-10 membrane (8 mL). The enzyme was then loaded on to S-200 gel-filtration column (400 mL column). The enzyme was eluted with buffer A with a flow rate of 0.8 mL/min. With these steps the enzyme was purified more than 150-fold with a specific activity of 13.9 units/mg protein (table 3). The unit is defined as μmole of product formed/min/mg of protein. The enzyme is a dimeric protein with a molecular weight of ~154,000 daltons with a subunit molecular weight of 45,000 daltons, as determined by SDS-PAGE.

TABLE 3

Purification of CBZ-Deprotecting Enzyme

| Step | Volume mL | Activity U/mL | Protein mg/mL | Sp.Activ. U/mg | Purification fold |
| --- | --- | --- | --- | --- | --- |
| Cell Extract | 500 | 0.142 | 1.8 | 0.08 | 1.00 |
| DE52-Flow Through | 700 | 0.183 | 0.58 | 0.32 | 4.00 |
| Ammonium Sulfate Precipitation | 60 | 2.496 | 7.45 | 0.34 | 4.25 |
| Phenylsepharose column | 28 | 0.117 | 0.13 | 0.90 | 11.41 |
| S-200 Gel-filtration column | 7 | 0.139 | 0.01 | 13.90 | 176.20 |

The purified enzyme prepared as described in this section has been used to deprotect CBZ-containing compounds as shown in table 4.

TABLE 4

| Substrate | Product | % Conversion |
| --- | --- | --- |
| Compound A | Compound B | 100 |
| CBZ-L-Phenylalanine | L-phenylalanine | 100 |

EXAMPLE 6

Enzymatic Deprotection of 250 mg Prep Batch of Compound A

The cell extract was prepared as described in the above section. To a 250 mL of cell extract, 250 mg Compound A was added and incubated at 28° C. and 95 rpm. After 40 hours of reaction, 250 mL of acetonitrile was added. The substrate and the product were analyzed by HPLC. The molar yield for Compound B was 87%.

EXAMPLE 7

Enzymatic Deprotection of CBZ-Containing Compounds

The cell extract prepared as described in the earlier section from *Sphingomonas paucimobilis* ATCC 202027 was used to deprotect [(3S)-Hexahydro-2-oxo-1-[2-oxo-2-(1-pyrrolidinyl)ethyl]-1H-azepin-3-yl]carbamic acid, phenylmethyl ester (Compound C) resulting in the formation of (S)-1-[(3-Aminohexahydro-2-oxo-1H-azepin-1-yl)acetyl]pyrrolidine (Compound D).

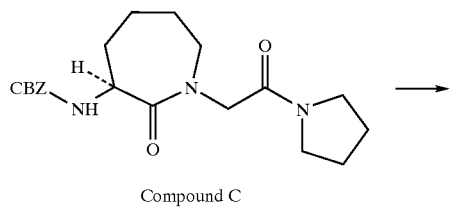

Compound C

-continued

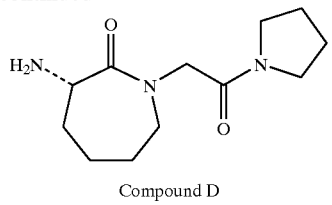

Compound D

EXAMPLE 8

Enzymatic Deprotection of CBZ-Containing Compounds

The cell extract prepared as described in the earlier section from *Sphingomonas paucimobilis* ATCC 202027 was used to deprotect 6-[(phenylmethoxy)carbonyl]amino]hexahydro-2,2-dimethyl-7-oxo-1H-azepine-1-acetic acid, ethyl ester hydrochloride 1 to 6-Aminohexahydro-2,2-dimethyl-7-oxo-1H-azepine-1-acetic acid, ethyl ester, hydrochloride (Compound E).

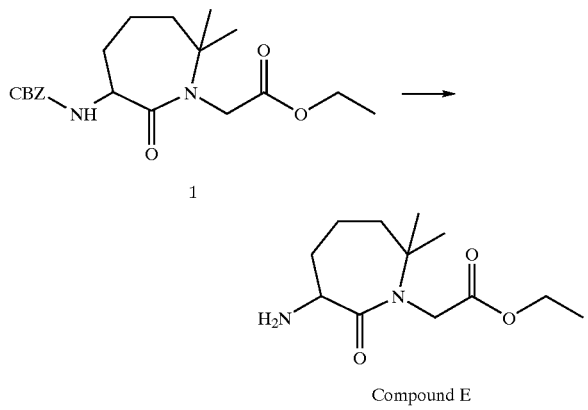

Compound E

Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of deprotecting a hydroxide or amine protected with a group of formula

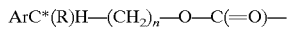

ArC*(R)H—(CH$_2$)$_n$—O—C(=O)— wherein R is H or independently the same as Ar, and n is 0 or 1–4, Ar refers to aromatic or heteroaromatic ring with 5 to 6 ring atoms and wherein the heteroaromatic ring contains one to two heteroatoms selected from O, N or S, which can be substituted with amino, alkanoyloxy, alkoxy, alkyl, alkylamino, allyl, carboxy, cycloalkyl, halo, haloalkyl, hydroxy, hydroxyalkyl or nitro, or up to one group which is (i) Ar* which is independently the same as Ar except that it is not substituted with a further aryl, (ii) Ar*-alkyl- or (iii) Ar*O—, a ring atom of adjacent to C* can be substituted with —CH$_2$—, —O—, —NH—, —S(O)$_q$— or —P(O)$_r$—, to form a bridge to corresponding position on R when R is Ar, q is 0 or 1–2 and r is 0 or 1–2, the method comprising:

contacting the protected hydroxide or amine with an enzyme effective to directly remove the protecting group; and recovering the amine.

2. The method of claim 1, wherein the protecting group is a phenylmethyloxycarbonyl group, which can be substituted.

3. The method of claim 1, wherein n is 0 when R is H.

4. The method of claim 1, wherein n is 1 where R is the same as Ar.

5. The method of claim 1, wherein the protected compound is an amine which is alanine, valine, leucine, isoleucine, proline, 4-hydroxyproline, phenylalanine, tryptophan, methionine, glycine, serine, homoserine, threonine, cysteine, homocysteine, tyrosine, asparagine, glutamine, aspartic acid, glutamic acid, lysine, α-amino-ε-caprolactam (lysine lactam), ε-methyllysine, ornithine, arginine, histidine or 3-methylhistidine, or any of the foregoing substituted on an alkyl portion thereof with hydroxy or alkyl, on an amino with up to one alkyl, or on a phenyl moiety with alkyl, alkanoyloxy, alkoxy, amino, carboxy, cycloalkyl halo, hydroxy, Ar* or Ar*O—, or a derivative of the foregoing forming a portion of a larger molecule via bonds formed by dehydration reactions with the amine or carboxylic acid moieties, or by carbon-nitrogen bonds formed at the amine moieties.

6. The method of claim 5, wherein the amine is α-amino-ε-caprolactam or α-amino-δ,δ-dimethyl-ε-caprolactam, or a derivative thereof.

7. The method of claim 6, wherein the protecting group a phenylmethyloxycarbonyl group, which can be substituted.

8. The method of claim 1, wherein the contacting effectuates the following reaction:

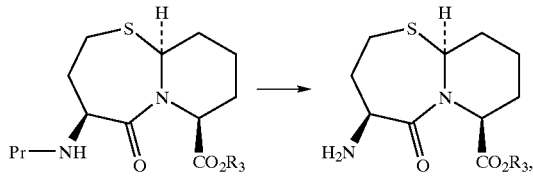

wherein Pr— is ArC*(R)H—(CH$_2$)$_n$—O—C(=O)—.

9. The method of claim 8, wherein the reaction is:

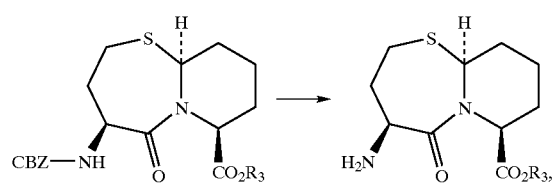

wherein CBZ- is N-carbobenzyloxy.

10. The method of claim 1, wherein the contacting effectuates the following reaction:

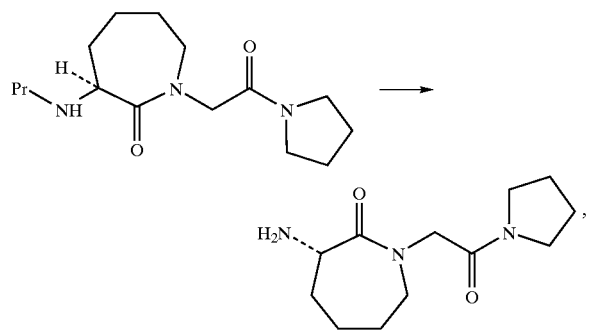

wherein Pr— is ArC*(R)H—(CH$_2$)$_n$—O—C(=O)—.

11. The method of claim 10, wherein the reaction is:

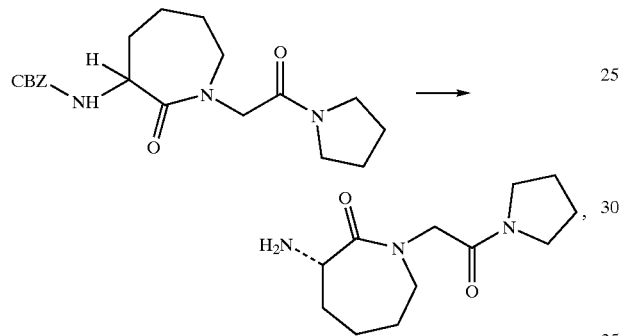

wherein CBZ- is N-carbobenzyloxy.

12. The method of claim 1, wherein the contacting effectuates the following reaction:

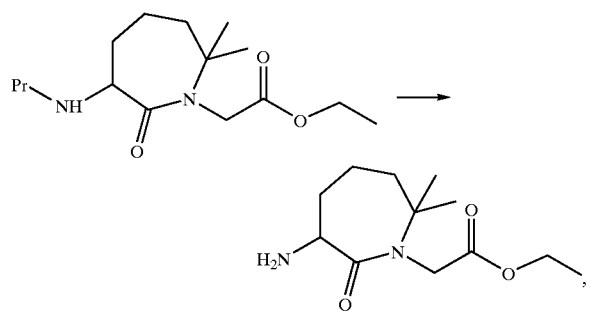

wherein Pr— is ArC*(R)H—(CH$_2$)$_n$—O—C(=O)—.

13. The method of claim 12, wherein the reaction is:

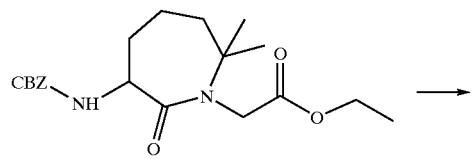

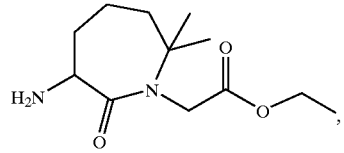

wherein CBZ- is N-carbobenzyloxy.

14. A method of resolving a racemic mixture of a compound having a hydroxyl or amino moiety that is directly bonded to a chiral carbon, the method comprising:

providing a derivative of the compound in which the hydroxide or amine protected with a group of formula ArC*(R)H—(CH2)$_n$—O—C(=O)—, wherein R is H or independently the same as Ar, and n is 0 or 1–4, Ar refers to an aromatic or heteroaromatic ring with 5 to 6 ring atoms and wherein the heteroaromatic ring contains one to two heteroatoms selected from O, N or S, which can be substituted with amino, alkanoyloxy, alkoxy, alkyl, alkylamino, allyl, carboxy, cycloalkyl, halo, haloalkyl, hydroxy, hydroxyalkyl or nitro, or up to one group which is (i) Ar* which is independently the same as Ar except that it is not substituted with further aryl, (ii) Ar*-alkyl- or (iii) Ar*O—, a ring atom of Ar adjacent to C* can be substituted with —CH$_2$—, —O—, —NH—, —S(O)$_q$— or —P(O)$_r$—, to form a bridge to a corresponding position on R when R is Ar, q is 0 or 1–2 and r is 0 or 1–2;

contacting the protected compound with an enzyme effective to directly remove the protecting group; and isolating the compound or protected derivative thereof in a composition that is enantiomerically enriched in the desired enantiomer.

15. The method of claim 14, wherein the enzyme is obtained from *Sphingomonas paucimobilis*.

16. The method of claim 14, wherein the enzyme is obtained from *Sphingomonas paucimobilis* strain ATCC 202027.

17. A method of deprotecting a hydroxide or amine protected with a group of formula ArC*(R)H—(CH$_2$)$_n$—O—C(=O)— wherein R is H or independently the same as Ar, and n is 0 or 1–4, Ar refers to aromatic or heteroaromatic ring with 5 to 6 ring atoms and wherein the heteroaromatic ring contains one to two heteroatoms selected from O, N or S, which can be substituted with amino, alkanoyloxy, alkoxy, alkyl, alkylamino, allyl, carboxy, cycloalkyl, halo, haloalkyl, hydroxy, hydroxyalkyl or nitro, or up to one group which is (i) Ar* which is independently the same as Ar except that it is not substituted with a further aryl, (ii) Ar*-alkyl- or (iii) Ar*O—, a ring atom of adjacent to C* can be substituted with —CH$_2$—, —O—, —NH—, —S(O)$_q$— or —P(O)$_r$—, to form a bridge to corresponding position on R when R is Ar, q is 0 or 1–2 and r is 0 or 1–2, the method comprising:

contacting the protected hydroxide or amine with an enzyme effective to remove the protecting group, wherein the enzyme is obtained from *Sphingomonas paucimobilis*; and recovering the amine.

18. The method of claim 17, wherein the protecting group is a phenylmethyloxycarbonyl group, which can be substituted.

19. The method of claim 17, wherein n is 0 when R is H.

20. The method of claim 17, wherein n is 1 where R is the same as Ar.

21. The method of claim 17, wherein the contacting effectuates the following reaction:

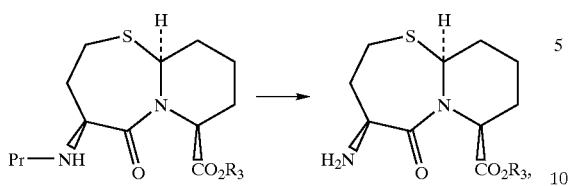

wherein Pr— is ArC*(R)H—(CH$_2$)$_n$—O—C(=O)—.

22. The method of claim 21, wherein the reaction is:

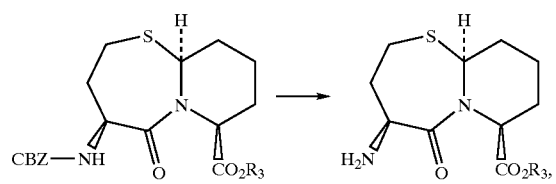

wherein CBZ- is N-carbobenzyloxy.

23. The method of claim 17, wherein the contacting effectuates the following reaction:

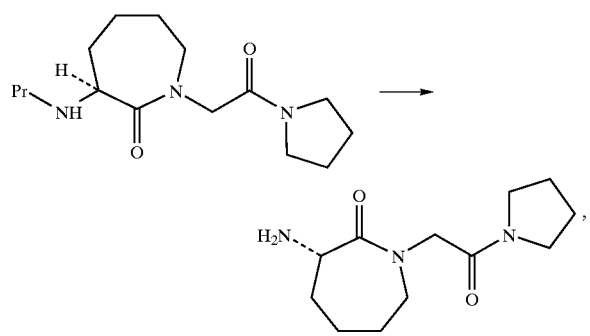

wherein Pr— is Ar*(R)H—(CH$_2$)—O—C(=O)—.

24. The method of claim 23, wherein the reaction is:

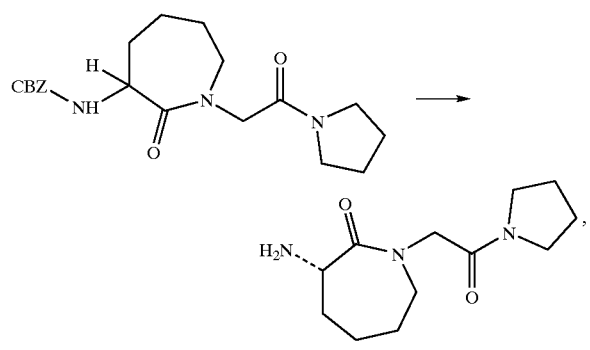

wherein CBZ- is N-carbobenzyloxy.

25. The method of claim 17, wherein the contacting effectuates the following reaction:

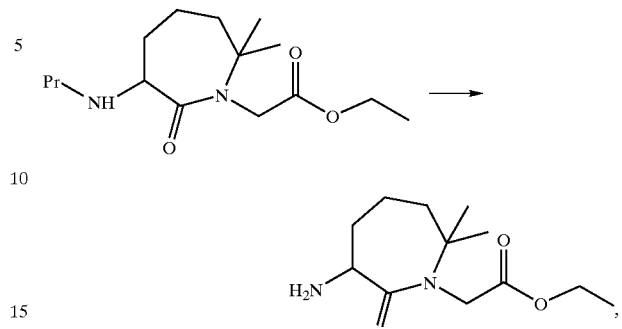

wherein Pr— is ArC*(R)H—(CH$_2$)$_n$—O—C(=O)—.

26. The method of claim 25, wherein the reaction is:

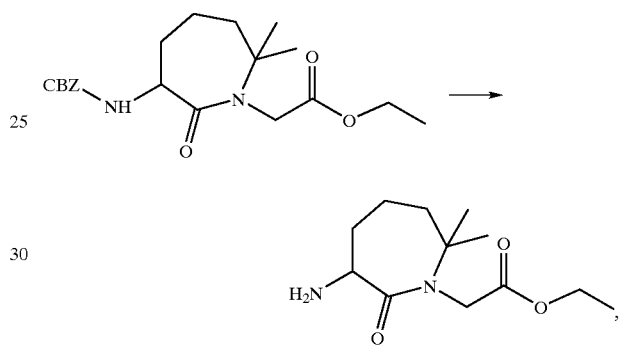

wherein CBZ- is N-carbobenzyloxy.

27. A method of deprotecting a hydroxide or amine protected with a group of formula

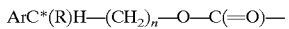

ArC*(R)H—(CH$_2$)$_n$—O—C(=O)— wherein R is H or independently the same as Ar, and n is 0 or 1–4, Ar refers to an aromatic or heteroaromatic ring with 5 to 6 ring atoms and wherein the heteroaromatic ring contains one to two heteroatoms selected from O, N or S, which can be substituted with amino, alkanoyloxy, alkoxy, alkyl, alkylamino, allyl, carboxy, cycloalkyl, halo, haloalkyl, hydroxy, hydroxyalkyl or nitro, or up to one group which is (i) Ar* which is independently the same as Ar except that it is not substituted with a further aryl, (ii) Ar*-alkyl- or (iii) Ar*O—, a ring atom of Ar adjacent to C* can be substituted with —CH$_2$—, —O—, —NH—, —S(O)$_q$— or —P(O)$_r$—, to form a bridge to a corresponding position on R when R is Ar, q is 0 or 1–2 and r is 0 or 1–2, the method comprising:

contacting the protected hydroxide or amine with an enzyme effective to remove the protection group, wherein the enzyme is obtained from *Sphingomonas paucimobilis* strain ATCC 202027; and recovering the amine.

* * * * *